(12) United States Patent
Walak

(10) Patent No.: US 6,890,350 B1
(45) Date of Patent: May 10, 2005

(54) COMBINATION SELF-EXPANDABLE, BALLOON-EXPANDABLE ENDOLUMINAL DEVICE

(75) Inventor: Steven E. Walak, Natick, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 132 days.

(21) Appl. No.: 09/702,226

(22) Filed: Oct. 31, 2000

Related U.S. Application Data

(63) Continuation-in-part of application No. 09/362,261, filed on Jul. 28, 1999, now Pat. No. 6,485,507.

(51) Int. Cl.[7] .................................................. A61F 2/06
(52) U.S. Cl. ...................... 623/1.15; 623/1.18; 623/1.44
(58) Field of Search ............................... 623/1.15, 1.18, 623/1.2, 1.44, 1.45, 1.46, 1.11

(56) References Cited

U.S. PATENT DOCUMENTS

| | | | |
|---|---|---|---|
| 5,019,090 A | 5/1991 | Pinchuk | |
| 5,135,536 A | 8/1992 | Hillstead | |
| 5,197,978 A | 3/1993 | Hess | |
| 5,282,824 A | 2/1994 | Gianturco | |
| 5,292,331 A | 3/1994 | Boneau | |
| 5,383,892 A | 1/1995 | Cardon et al. | |
| 5,395,308 A | 3/1995 | Simon et al. | |
| 5,395,390 A | 3/1995 | Simon et al. | |
| 5,507,767 A | 4/1996 | Maeda et al. | |
| 5,709,704 A | 1/1998 | Nott et al. | |

(Continued)

FOREIGN PATENT DOCUMENTS

| | | | |
|---|---|---|---|
| EP | 0 689 807 | 1/1996 | |
| EP | 0 951 877 | 10/1999 | |

(Continued)

OTHER PUBLICATIONS

U.S. Appl. No. 09/442,165, filed Nov. 17, 1999, Chouinard et al.

(Continued)

*Primary Examiner*—Corrine McDermott
*Assistant Examiner*—William H Matthews
(74) *Attorney, Agent, or Firm*—Vidas, Arrett & Steinkraus, P.A.

(57) ABSTRACT

An endoluminal device, such as a stent or a vena cava filter, comprising at least one superelastic section and at least one plastically deformable section. The superelastic section may comprise, for example, a superelastic grade of nitinol, whereas the plastically deformable section may comprise, for example, gold, platinum, tantalum, titanium, stainless steel, tungsten, a nickel alloy, a cobalt ally, a titanium alloy, or a combination thereof. Each plastically deformable section may merely comprise a constrained portion of the superelastic section comprising a plastically deformable material, such as gold. The device enables deployment by a method comprising introducing the device into a body lumen with the device radially constrained in a first configuration having a first diameter; allowing the device to self-expand into a second configuration having a second diameter less than or equal to a fully-self-expanded diameter; and then optionally "fine-tuning" the device by forcibly expanding the device into a third configuration having a third diameter in a range between the second diameter and less than or equal to a fully-forcibly-expanded diameter. The superelastic and plastically deformable sections may be tubular sections placed end-to-end, such that the plastically deformable section can be conformed to fit a tapered section of a lumen.

22 Claims, 11 Drawing Sheets

U.S. PATENT DOCUMENTS

| | | | |
|---|---|---|---|
| 5,725,570 A | | 3/1998 | Heath |
| 5,800,515 A | | 9/1998 | Nadal et al. |
| 5,815,904 A | | 10/1998 | Clubb et al. |
| 5,836,969 A | | 11/1998 | Kim et al. |
| 5,858,556 A | | 1/1999 | Eckert et al. |
| 5,868,783 A | | 2/1999 | Tower |
| 5,938,697 A | | 8/1999 | Killion et al. |
| 5,980,566 A | | 11/1999 | Alt et al. |
| 6,093,157 A | * | 7/2000 | Chandrasekaran .......... 600/585 |
| 6,120,534 A | | 9/2000 | Ruiz |
| 6,217,607 B1 | * | 4/2001 | Alt .............................. 606/192 |
| 6,241,762 B1 | | 6/2001 | Shanley |
| 6,293,967 B1 | | 9/2001 | Shanley |
| 6,425,855 B2 | | 7/2002 | Tomonto |

FOREIGN PATENT DOCUMENTS

| | | | | |
|---|---|---|---|---|
| WO | WO 95/31945 | * | 11/1995 | ............. A61F/2/06 |
| WO | WO 00/50100 | | 8/2000 | |
| WO | WO 01/08600 | | 2/2001 | |

OTHER PUBLICATIONS

U.S. Appl. No. 09/227,407, filed Jan. 8, 1999, Taskovics et al.

U.S. Appl. No. 09/362,261, filed Jul. 28, 1999, Walak et al.

"Specifying NiTi Materials," Sep. 12, 2000, www.sma–inc.com/SpecifyingNiTi.html.

Copy of Invitation to Pay Additional Fees with Annex to Form PCT/ISA/206 Communication Relating to the Results of the Partial International Search (dated Apr. 18, 2002).

* cited by examiner

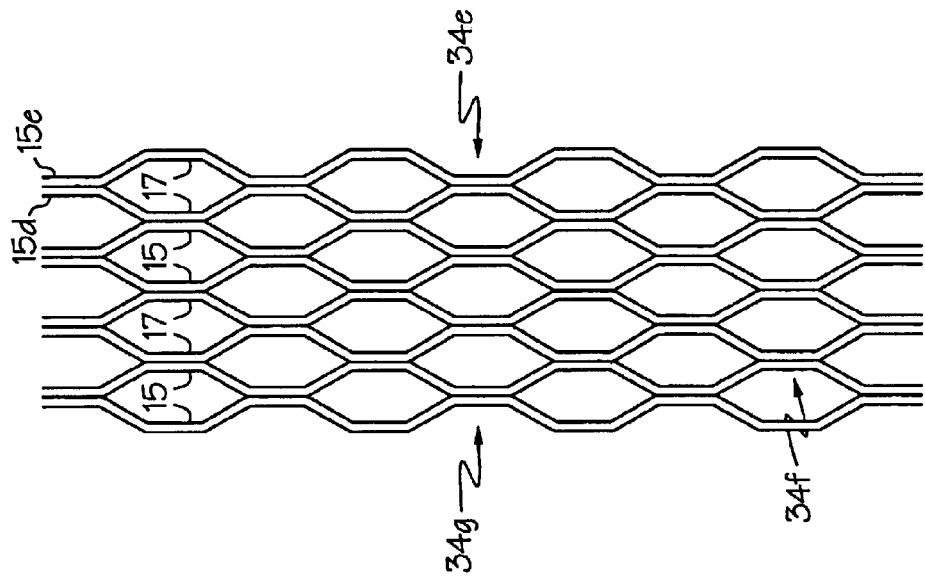
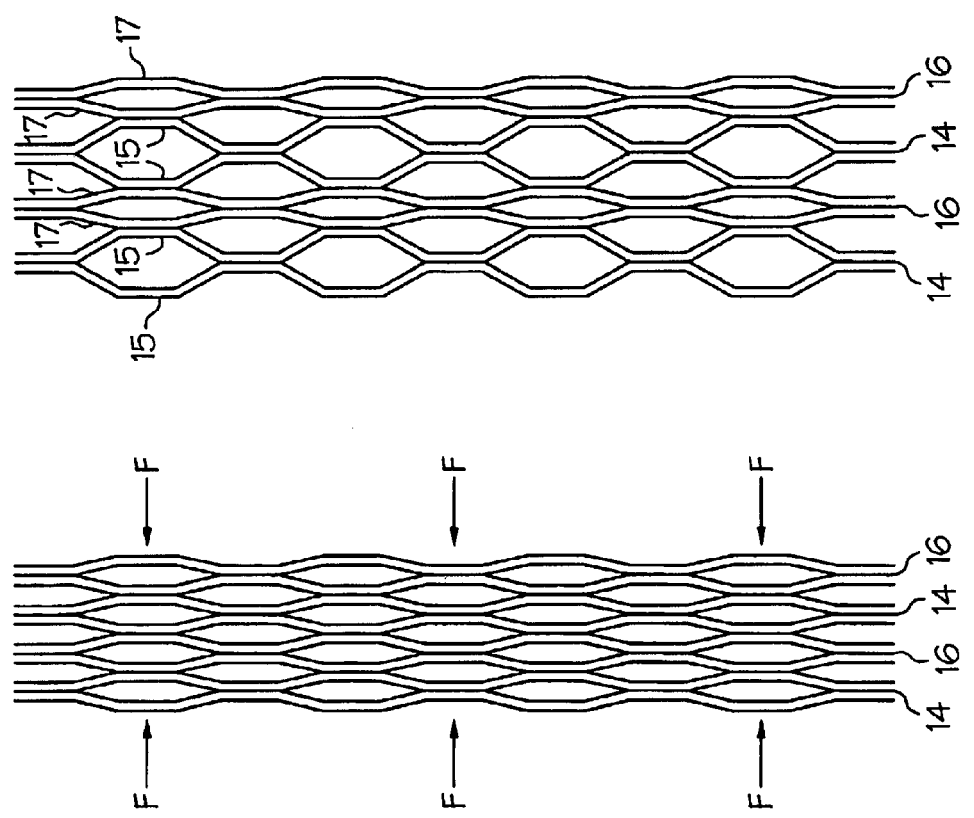
FIG. 4A  FIG. 4B  FIG. 4C

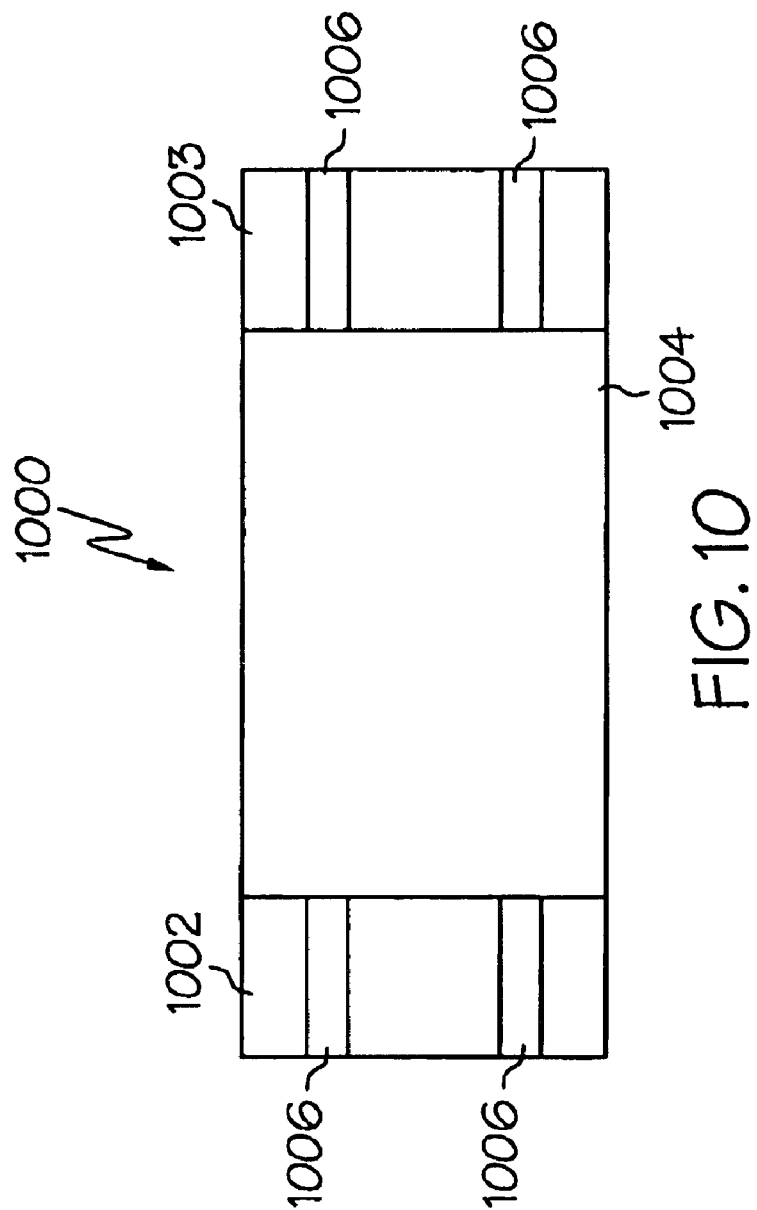

COMBINATION SELF-EXPANDABLE, BALLOON-EXPANDABLE ENDOLUMINAL DEVICE

CROSS-REFERENCE TO RELATED APPLICATIONS

This application is a continuation-in-part of U.S. patent application Ser. No. 09/362,261, filed July 28, 1999, now U.S. Pat. No. 6,485,507 the contents of which is incorporated herein in its entirety by reference.

TECHNICAL FIELD

This invention relates generally to endoluminal devices such as vena cava filters, stents, grafts, and/or prostheses and, more specifically, to endoluminal devices that have combined self-expanding and balloon-expandable properties.

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endoluminally, i.e. by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

A vena cava filter is an implantable filter, typically implanted in a patient's inferior vena cava using minimally invasive techniques, for reducing the risk of arterial plaques dislodged during surgery or clots formed in the bloodstream from becoming lodged in and partially or completely blocking vessels supplying blood and oxygen to critical organs, such as the heart, lungs and brain. Such filters enable dangerous blood clots to be removed from circulation and held in a safe location until they can be dissolved by medication or extracted, again using minimally invasive techniques. Conventional implantable blood filters employing a variety of geometrics are known, but may are generally basket or cone shaped to provide adequate clot-trapping area while permitting sufficient blood flow. Also known are filters formed of various loops of wire, including some designed to partially deform the vessel wall in which they are implanted.

Typically, endoluminal devices such as vena cava filters and stents expand by one mechanism or another, not by some combination. That is, balloon expandable devices are not also self-expanding, and self-expanding devices are not typically balloon expandable. While it is known to "model" self-expanding stents to conform to anatomy in which the stent has been deployed to a shape suitable for accepting the stent, such modeling does not vary the diameter of the stent, but rather varies the anatomy. For example, a self-expanding stent deployed in an artery having a plaque deposit on the walls may be modeled to crush the plaque deposit down.

Self-expanding devices typically are known for excellent crush resistance, potential for longitudinal flexibility, for exerting a constant outward force to maintain an open vessel, and for having the capacity to elastically expand and contract with the blood vessel. On the other hand, self-expanding devices typically must be sized accurately to provide acceptable outward force and cannot generally be manipulated to a larger diameter after deployment. Self-expanding devices are typically made of a superelastic material, such as a superelastic grade of nitinol, which has a limited x-ray visibility.

Balloon-expandable devices are typically capable of expansion into a range of sizes, and typically are relatively stiff and inflexible. Balloon-expandable devices do not typically recover if crushed in the body, however, and are rigid bodies that do not expand and contract with motion of the vessel. Balloon-expandable devices are also typically longitudinally rigid, limiting delivery through tortuous anatomy. Balloon-expandable devices are made of a plastically deformable metal such as stainless steel, platinum, or a plastically deformable grade of nitinol.

In light of the advantages and disadvantages of self-expanding and balloon-expandable technologies as currently known, there is a need in the art for technology bridging the advantages of both.

SUMMARY OF THE INVENTION

It is to be understood that both the foregoing general description and the following detailed description are exemplary, but are not restrictive, of the invention. The invention comprises an endoluminal device, such as a stent or a vena cava filter, comprising at least one superelastic section and at least one plastically deformable section. The device typically has a first constrained diameter, a second fully-self-expanded diameter, and a third fully-forcibly-expanded diameter, wherein the third diameter is greater than the second diameter and the second diameter is greater than the first diameter.

The device may comprise a plurality of filaments including one or more superelastic filaments and one or more plastically deformable filaments, particularly where one or more of the superelastic filaments extends longitudinally substantially parallel to one or more of the plastically deformable filaments along the length of the stent. In the alternative, each superelastic section and/or each plastically deformable section may comprise a sheet or a longitudinally severed tube cut by a laser or other precision cutting mechanism.

Each superelastic filament may be connected along one or more longitudinal portions thereof to another superelastic filament, another columnar unit of the same superelastic filament, one or more plastically deformable filaments, or a combination thereof. Similarly, each plastically deformable filament may be connected along one or more longitudinal portions thereof to another plastically deformable filament, another columnar unit of the same plastically deformable filament, one or more superelastic filaments, or a combination thereof. The longitudinal portions may be connected at a joint by brazing, welding, adhesive bonding or suturing.

The superelastic filament or filaments preferably comprise a superelastic grade of nitinol, such as thermal shape memory nitinol. The plastically deformable filament or filaments preferably comprise gold, platinum, tantalum, titanium, stainless steel, tungsten, a cobalt alloy, a nickel alloy, a titanium alloy, or a combination thereof, such as a plastically deformable grade of nitinol or a composite nitinol wire having a core of a plastically deformable material (hereinafter referred to as a "deformable core nitinol composite").

Each plastically deformable section may comprise a constrained portion of the superelastic section comprising a plastically deformable material, such as gold. For example, the constrained portion may comprise a combination of superelastic material and plastically deformable material, such as plastically deformable material plated onto superelastic material, a plastically deformable hypotube overlaid onto superelastic material, plastically deformable material ion implanted within superelastic material, or a composite of deformable material and superelastic material. In particular, the device may be cut from a composite comprising a sandwich having outer layers of nitinol and inner longitudinal or transverse strips of plastically deformable material. In an alternative embodiment, the device may comprise one or more hoops in a zig-zag configuration of oppositely-pointing apex sections, where the plastically deformable sections comprise one or more apex sections comprising plastically deformable material. The plastically deformable apex sections on each of said hoops may be longitudinally aligned.

The device may also comprise a first tubular section comprising a superelastic section and a second tubular section comprising a plastically deformable section. Where the first and second tubular sections both comprise a combination of superelastic material and plastically deformable material, the plastically deformable section has a ratio of plastically deformable material to superelastic material that is greater than the ratio of plastically deformable material to superelastic material in the superelastic section. The device may comprise a plastically deformable section mounted between two superelastic sections each having different fully-self-expanded diameters, so that the device can be mounted in a tapered lumen and forcibly expanded to conform to the taper in the lumen in accordance with a method of this invention.

The invention also comprises a method of deploying an endoluminal device of this invention in a body lumen. The method comprises introducing the device into the body lumen with the device radially constrained in a first configuration having the first diameter; allowing the device to self-expand into a second configuration having a diameter less than or equal to the second diameter; and optionally forcibly expanding at least a portion of the device into a third configuration having a diameter greater than the second diameter and less than or equal to the fully-expanded diameter.

Where the device comprises a plastically-deformable tubular section and a superelastic tubular section, the method may comprise deploying the device in a lumen having a tapered portion. In such case, the method further comprises introducing the device with the device radially constrained in a first configuration in which each tubular section has a first diameter. Next, the device is allowed to expand such that the plastically deformable section aligns with the tapered portion of the lumen. Thus, the device self-expands into a second configuration in which the superelastic section has a second diameter greater than the first diameter and less than or equal to the fully-self-expanded diameters. The device is finally forcibly expanded into a third configuration in which the plastically deformable section has a variable diameter that conforms to the tapered section of the lumen.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 4A is a side view illustration of an exemplary filamentary stent of the present invention cut longitudinally and laid flat, comprising a plurality of superelastic and plastically deformable filaments, in a constrained configuration.

FIG. 4B is a side view illustration of the exemplary filamentary stent of FIG. 4A in a fully-self-expanded configuration.

FIG. 4C is a side view illustration of the exemplary filamentary stent of FIG. 4A in a fully-forcibly-expanded configuration.

FIG. 10 is a side view illustration of an exemplary prosthesis comprising plastically deformable elements only at opposite ends of the stent.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Although the term "vena cava filter" technically refers to implantable filters placed in the vena cava—the jugular or femoral veins, which are the typical locations for such filters—the term as used herein refers to any type of implantable filter, regardless of the specific body lumen into which it is implanted. In particular, the anchoring assemblies or portions of vena cava filters shown in U.S. Pat Nos. 5,709, 704 and 5,836,939 may be particularly well-suited for construction in accordance with this invention. Vena cava filters are deployed much in the same way as stents, and thus throughout this application the term "endoluminal device" is used to refer to both vena cava filters and stents. In many instances, however, examples refer specifically to stents, but should not be interpreted to be limited to stents alone. Thus, discussion of aspects of this invention with respect to stents should also be considered applicable to implantable filters and vice versa, where applicable.

Figure 1:
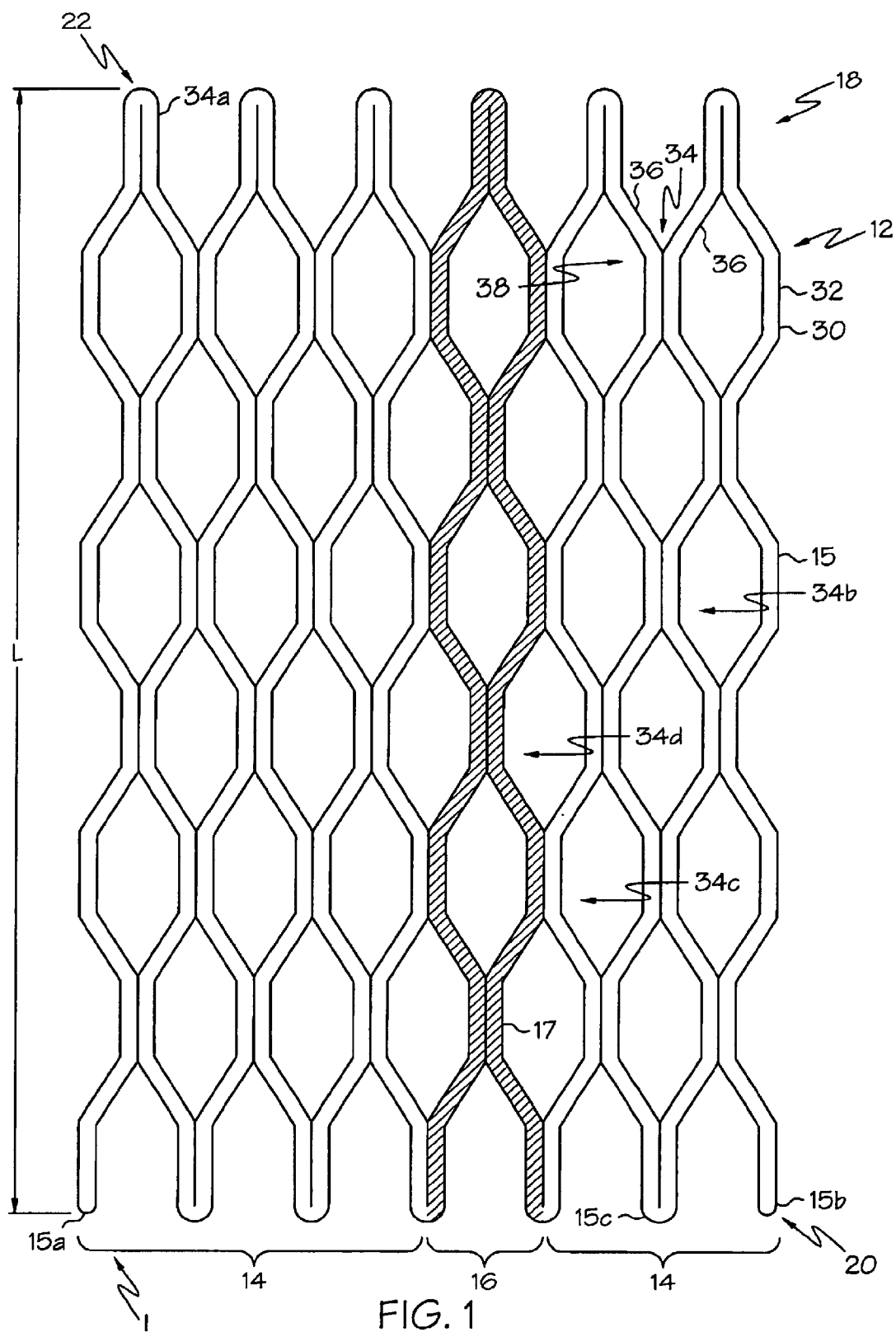
FIG. 1 is a side view illustration of an exemplary filamentary stent of the present invention cut longitudinally and laid flat, consisting of two filaments.

FIG. 1 shows an exemplary stent embodiment according to the present invention wherein the tubular stent has been cut along a line parallel to the tubular stent axis and flattened. The architecture of stent 12 shown in FIG. 1 is substantially similar to the architectures described in U.S. Pat. Nos. 5,354,308 and 5,395,390 to Simon et al., which are incorporated herein by reference, and described further below. The structures described in the '308 and '390 Simon patents are merely examples of particular stents architectures, and are not intended to be limiting. Other U.S. patents and patent families claiming priority therefrom, incorporated herein by reference, that may be well-suited for use in this invention include:

5,019,090 Pinchuk 5,135,536 Hillstead 5,292,331 Boneau 5,282,824 Gianturco 5,354,308 Simon et al.

5,507,767 Maeda et al.

5,800,515 Nadal et al.

The above list of patents is only exemplary, not limiting, however, as any number of different stent architectures may be used to create stents in accordance with this invention.

Stent 12 comprises a plurality of filaments 15 and 17. Superelastic filaments 15 typically comprise a superelastic grade of nitinol, whereas plastically deformable filaments 17 typically comprise gold, platinum, tantalum, titanium, stainless steel, tungsten, a cobalt alloy, a nickel or titanium alloy, such as a plastically deformable grade of nitinol or deformable core nitinol composite, or a combination of any of the above. The filaments may in the alternative comprise bioabsorbable or biostable polymers, such as are known in the art.

As used herein, a "superelastic" material is one that may be deformed into a certain configuration without the material permanently taking on the deformed shape. For example, a thermal shape memory material may be deformed into a number of configurations, but will return to its memory shape upon temperature activation. A "plastically deformable" material, on the other hand, is a material that once deformed into a certain shape, keeps that shape indefinitely, until deformed again by some other force.

As described in the background section, stents are typically inserted into a body lumen from a remote location through an insertion point in the body through which an "introducer", containing the stent in a radially compressed configuration, is threaded and navigated through the body lumen to the deployment location, where the stent is deployed in a radially expanded configuration. As referred to herein, "distal" refers to the direction further away from the insertion point and "proximal" refers to the direction closer to the insertion point.

As shown in FIG. 1, stent 12 comprises a filamentary stent architecture having a plurality of polygonal, hexagonal cells 30 having as sides thereof straight axially-extending portions 32 joined together along a set of parallel lengths 34, the parallel lengths deviating from one another proximally and distally of each parallel length into diagonal lengths 36, such that each set of parallel lengths and attached diagonal lengths form a Y-shaped intersection 38. The polygonal cell stent architecture in stent 12 terminates at a set of parallel lengths 34a, which may be joined together by welding, brazing, or any means known in the art, and additionally may comprise a single filament merely bent 180 degrees back upon itself, as shown in FIG. 1. In the alternative, the ends may be wound into an end winding having a different stent architecture, such as is described in U.S. patent application Ser. No. 09/442,165, filed Nov. 16, 1999, assigned to the common assignee of the present invention, and incorporated herein by reference.

As shown in FIG. 1, stent 12 comprises two sections 14 and 16. Section 14 is a superelastic section and section 16 is a plastically deformable section. Each section 14 and 16 extends longitudinally along length L of the stent. As shown in FIG. 1, stent 12 consists of two filaments: superelastic filament 15 and plastically deformable filament 17. For ease of illustration in FIG. 1, stent 12 is shown after having been slit longitudinally and flattened, cutting filament 15 into two sections. When stent 12 is in its normal tubular form, however, filament ends 15a and 15b are connected to one another as part of continuous filament 15. For ease of identification, plastically deformable filament 17 is shown in FIG. 1 shaded in gray. Throughout the figures, gray shading is used to distinguish the plastically deformable elements from superelastic elements.

Stent 12 has opposite ends 18 and 20. Each filament 15 and 17 longitudinally traverses length L of stent 12 from the end 18 to the end 20 in a plurality of columnar units 22. As used herein, the term "columnar unit" refers to a single pass of the filament from one of ends 18 or 20 to the opposite end. Thus, as shown in FIG. 1, filament 15 comprises ten columnar units and filament 17 comprises two columnar units. In an alternative embodiment, each columnar unit, each pair of columnar units, or any number of columnar units may comprise a separate filament. Where each columnar unit is a separate filament, as shown in FIG. 4C, each superelastic filament 15 and each plastically deformable filament 17 extends only once between end 18 and end 20. Thus, stent 40 as shown in FIG. 4C comprises four superelastic filaments and four plastically deformable filaments. In such a case, ends 15$d$ and 15$e$, for example, may be welded, brazed, twisted, glued, sutured, or otherwise connected together by means other than by a 180-degree turn 15$c$ of a continuous wire, such as shown in FIG. 1.

As shown in FIG. 1, superelastic filament 17 extends longitudinally substantially axially parallel to plastically deformable filament 15 along length L of stent 12. As used herein, "substantially parallel" is used to denote that despite the serpentine bending of each filament about axis I, the axes of each columnar unit are essentially parallel to one another when the stent is in an unconstrained configuration. "Essentially parallel" is used to acknowledge that some minimal deviation from parallel may be possible.

Superelastic filament 15 is connected along one or more longitudinal portions thereof (each pair of parallel lengths 34) to either another columnar unit of the same superelastic filament, such as at 34$a$ or 34$b$, or to plastically deformable filament 17, such as at 34$c$. Similarly, plastically deformable filament 17 is connected along one or more longitudinal portions thereof to another columnar unit of the same plastically deformable filament, such as at 34$d$, or to superelastic filament 15, such as at 34$c$, or some combination thereof. Where the stent comprises multiple superelastic filaments 15 and multiple plastically deformable filaments 17, such as illustrated in FIG. 4C, each plastically deformable filament may be connected along one or more longitudinal portions thereof to another plastically deformable filament, such as at 34$e$, or to a superelastic filament, such as at 34$f$, and each superelastic filament may be connected along one or more longitudinal portions thereof to another superelastic filament, such as at 34$g$, or to a plastically deformable filament, such as at 34$f$.

The longitudinal portions of the filaments at each set of parallel lengths 34 may be connected to make a joint by any means known in the art, such as brazing, welding, adhesively bonding, or suturing. Welding, suturing, adhesive bonding, and brazing processes are well-known in the art. Where the joint is a welded joint, it is preferable that both the superelastic material and the plastically deformable material are grades of nitinol. A superelastic grade of nitinol is any grade that is in its Austenitic phase at the use temperature (essentially the temperature of the human body). A plastically deformable grade of nitinol is any grade that is in its Martenisic phase at the use temperature, such as Alloy M, manufactured by Shape Memory Application., of San Jose, Calif., having a typical Active Austenite Finish $A_f$ in the range of 45–95° C., or Alloys B ($A_f$ 45–80° C.) or BH ($A_f$ 80–120° C.), manufactured by Memry Corporation, of Brookfield, Conn. Deformable core nitinol composites are also plastically deformable nitinol materials. Where the joint is a brazed joint, the preferred superelastic material is nitinol and the preferred plastically deformable material is stainless steel, a titanium alloy, or platinum.

Figure 2:
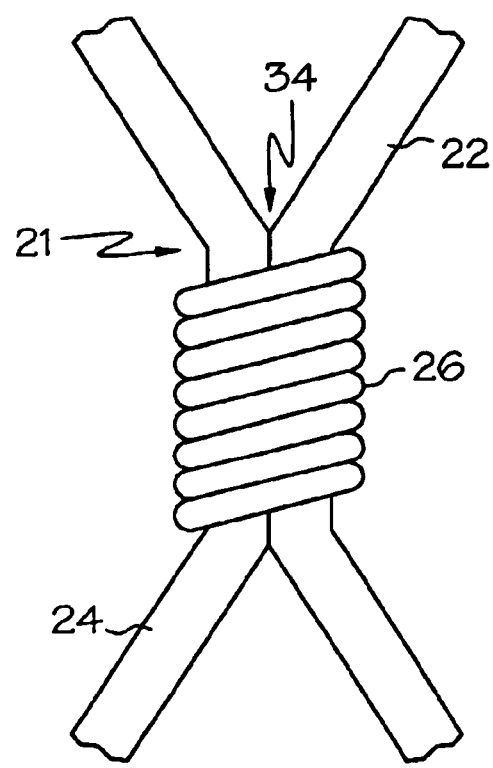
FIG. 2 is a side view illustration of an exemplary brazed joint.

A brazed joint may comprise any wire wrapped around the joint to provide mechanical support. An exemplary brazing method is described, below. As shown in FIG. 2, joint 21 comprises filaments 22 and 24 wrapped by coil 26. One of filaments 22 and 24 may be superelastic, and the other plastically deformable, or both filaments may be the same type of material. To form such a brazed joint, wires 22 and 24 are brought together so that they abut, and a brazing material, such as any standard brazing material known in the art, is melted to wet at least the portions of both wires that contact one another, and cooled to solidify. Coil 26 is then wrapped around the brazed, abutted filaments. Coil 26 may comprise a deformable metal or a thermal shape memory material, such as nitinol. Where a shape memory material is used, it may be first wound into a tight helical coil around a small diameter form and annealed to set its Austenite shape. It is then cooled to its Martensite configuration and unraveled to be re-coiled about the brazed, abutted filaments. A heating step then shrinks joining coil 26 back to its tight Austenite shape. A low-temperature brazing material may then be melted and solidified over the coil to fix the coil in its Austenite shape.

In the alternative, instead of a filamentary coil, a split hypotube may be annealed in a closed shape, cooled to its Martensite condition and opened to allow it to be slipped over abutted filaments 22 and 24, and heat shrunk back to its closed shape. The low temperature brazing material may then be used to seal the hypotube in the closed position.

Figure 3A:
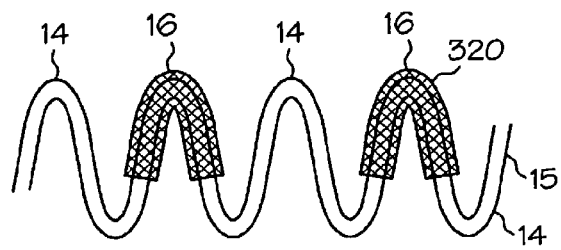
FIG. 3A is a side view illustration of an exemplary zig-zag stent hoop of the present invention cut longitudinally and laid flat, in a constrained configuration.
Figure 3B:
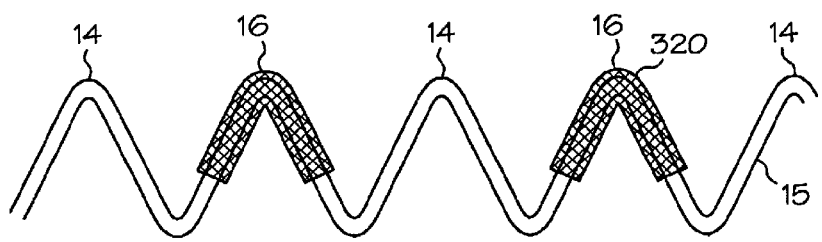
FIG. 3B is a side view illustration of the exemplary zig-zag stent hoop of FIG. 3A in a fully-self-expanded configuration.
Figure 3C:
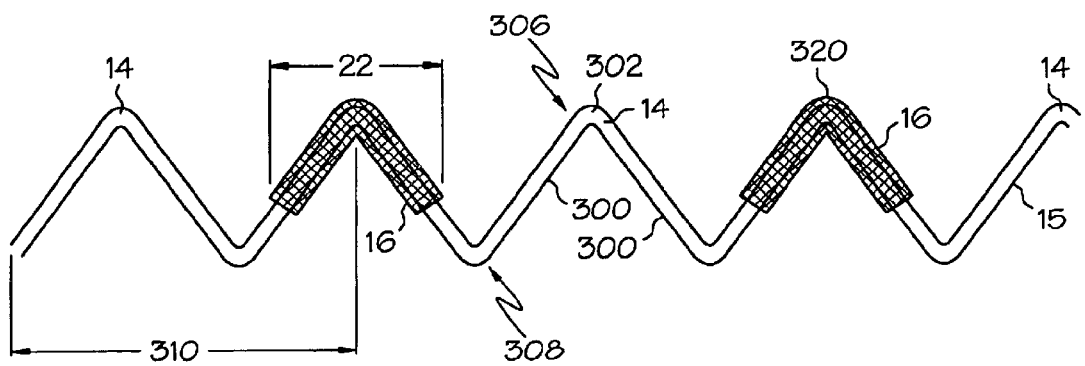
FIG. 3C is a side view illustration of the exemplary zig-zag stent hoop of FIG. 3A in a fully-forcibly-expanded configuration.

In an alternative embodiment, shown in FIGS. 3A–C, stent 30 may comprise a zig-zag stent architecture. As shown in FIG. 3C, a zig-zag stent architecture comprises a plurality of struts 300 joined at apex sections 302, with a plurality of alternating oppositely-pointed apex section arranged into cylindrical hoops, shown in FIGS. 3A–C after being longitudinally cut and flattened. Apex sections 302 pointing in a first direction can be referred to peaks 306 and apex sections pointing in the opposite direction can be referred to as valleys 308, with any circumferentially adjacent, oppositely pointing apex sections together with three adjacent struts 300 forming a zig-zag 310. The zig-zag architecture shown in FIG. 3 is merely one exemplary zig-zag embodiment, but is not intended to limit the invention thereto.

As shown in FIG. 3C, each plastically deformable section 16 comprises a constrained portion of superelastic section 14. Plastically deformable section 16 in FIG. 3C comprises a combination of plastically deformable material 320 and superelastic material (filament 15). FIG. 3C shows a single hoop in a zig-zag configuration, split and laid flat, of oppositely-pointing apex sections (peaks 306 and valleys 308), where each plastically deformable section 16 comprises a peak 306 comprising plastically deformable material. As shown in FIG. 3C, the combination comprises plastically deformable material overlying the superelastic material, such as made by plating deformable material, such as gold, onto the superelastic material, or by overlying a plastically deformable hypotube onto the superelastic material. The combination may instead comprise plastically deformable material ion implanted into superelastic material, or a composite of deformable material and superelastic material. Ion implantation processes are well-known in the art. A composite combination is described herein below.

Figure 6:
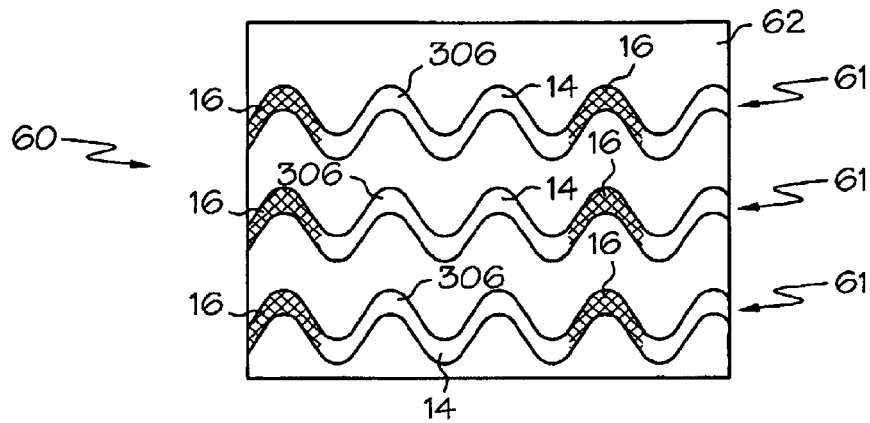
FIG. 6 is a side view illustration of an exemplary prosthesis cut longitudinally and laid flat, comprising a plurality of zig-zag stent hoops.

As shown in FIG. 6, a prosthesis 60 (shown split and laid flat) may comprise a plurality of stent hoops 61 attached to a graft 62, wherein peaks 306 on each hoop are longitudinally aligned with the peaks of the other hoops. The plastically deformable apex sections 16 on each of the hoops may then be longitudinally aligned with the plastically deformable apex sections on the other hoops.

Figure 4F:
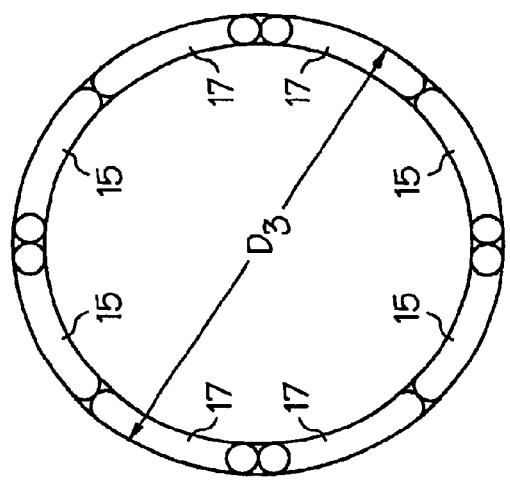
FIG. 4F is a top view illustration of the exemplary filamentary stent of FIG. 4A in the fully-forcibly-expanded configuration of FIG. 4C.
Figure 4E:
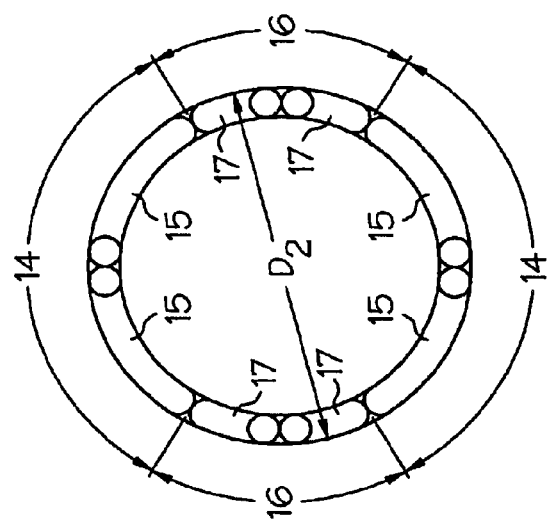
FIG. 4E is a top view illustration of the exemplary filamentary stent of FIG. 4A in the fully-self-expanded configuration of FIG. 4B.
Figure 4D:
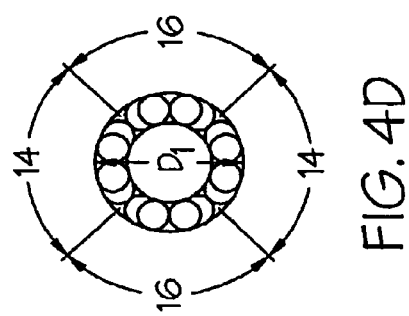
FIG. 4D is a top view illustration of the exemplary filamentary stent of FIG. 4A in the constrained configuration of FIG. 4A.
Figure 5C:
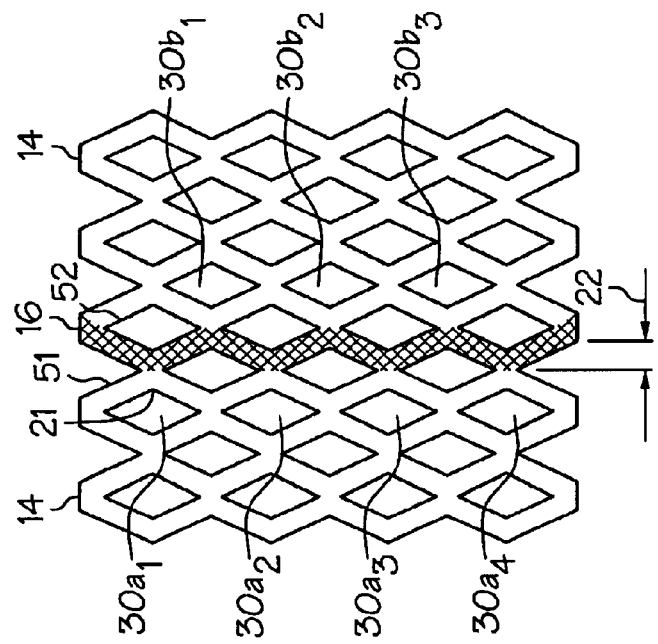
FIG. 5C is a side view illustration of the exemplary laser-cut stent of FIG. 5A in a fully-forcibly-expanded configuration.
Figure 5B:
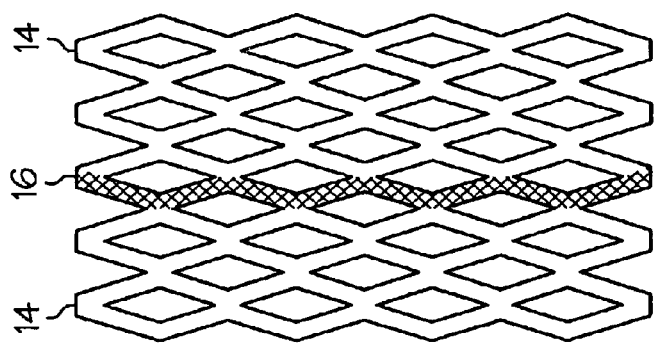
FIG. 5B is a side view illustration of the exemplary laser-cut stent of FIG. 5A in a fully-self-expanded configuration.
Figure 5A:
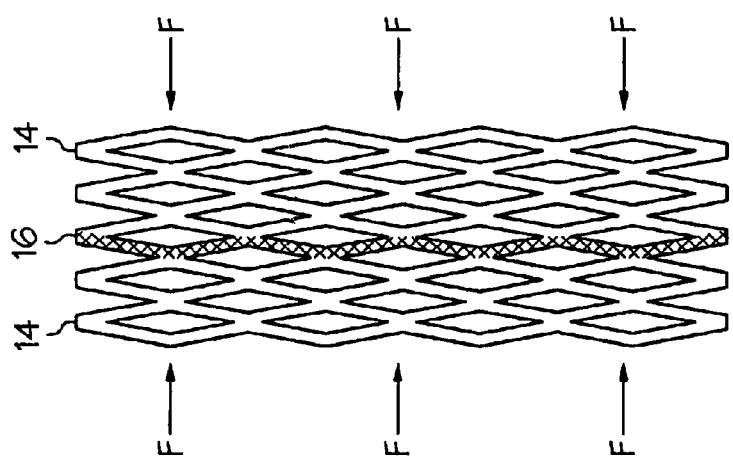
FIG. 5A is a side view illustration of an exemplary laser-cut stent of the present invention cut longitudinally and laid flat, in a constrained configuration.

Although shown as a filamentary stent in FIGS. 1–4F, stent 12 may also comprise, at least in part, a hypotube or sheet cut by precision cutting means such as a laser or chemical etching, as shown in FIGS. 5A–5C. While laser cutting is the most common such method for performing such a cutting step, as is known in the art, the structure is not limited to any particular cutting mechanism. As shown in FIG. 5C, superelastic section 14 of stent 50 comprises a laser-cut sheet or a longitudinally severed laser cut tube. The opposite edges 51 and 52 of superelastic section 14 are joined together by plastically deformable section 16. Plastically deformable section 16 may be a portion of a laser-cut sheet or longitudinally severed laser cut tube itself, in which each joint 21 between sections 14 and 16 may be attached by brazing, welding, adhesive bonding, or any method known in the art. Section 16 may instead be filamentary, such as for example, a filament having a zig-zag architecture stent (not shown) wound helically between edge-most cells 30a and edge-most cells 30b on adjacent opposite edges 51 and 52 of superelastic section 14. For example, the filament may be wound in order from cell $30a_1$ to $30b_2$ to $30a_2$ to $30b_2$ to $30a_3$ to $30b_3$ to $30a_4$ and optionally back again to cell $30a_1$ through all of the same cells in reverse order.

As shown in FIG. 5C, plastically deformable section 16 comprises at least one columnar unit 22 having a longitudinal zig-zag configuration disposed between opposite longitudinal edges 51 and 52 of single superelastic section 14. Where there are multiple superelastic sections 14, each plastically deformable section may be disposed between two superelastic sections, and each superelastic section may be disposed between two plastically deformable sections.

Figure 7A:
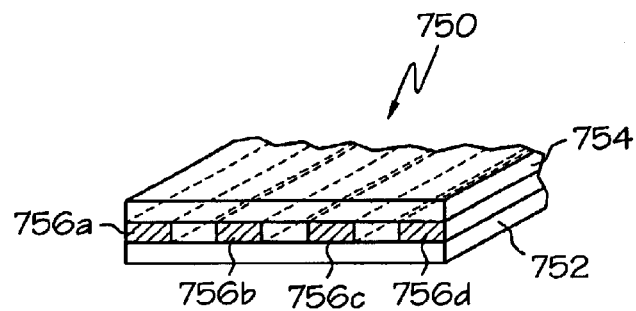
FIG. 7A is a perspective view of an exemplary composite sheet having continuous longitudinal stripes of plastically deformable material, used for making an exemplary stent embodiment of the present invention.
Figure 7B:
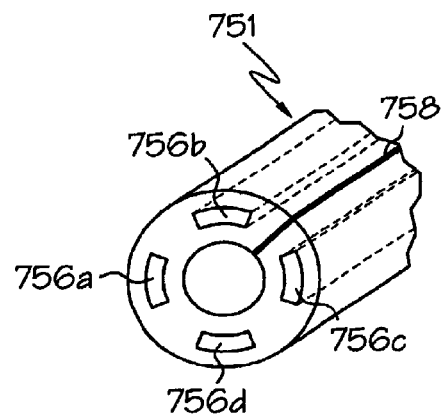
FIG. 7B is a perspective view of a tube formed from the composite sheet of FIG. 7A, after a rolling step.
Figure 7C:
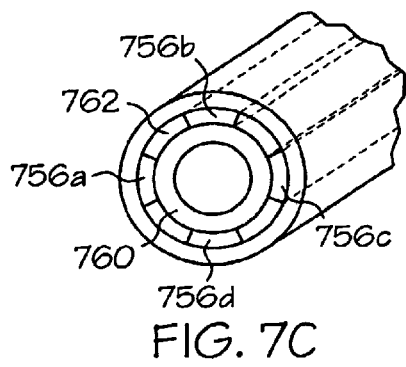
FIG. 7C is a perspective view of a composite tube comprising an inner and outer hypotube.
Figure 7D:
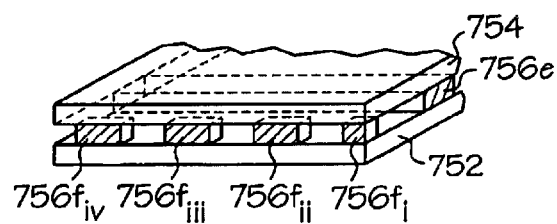
FIG. 7D is a perspective view of an exemplary composite sheet having transverse stripes of plastically deformable material, used for making an exemplary stent embodiment of the present invention.
Figure 7E:
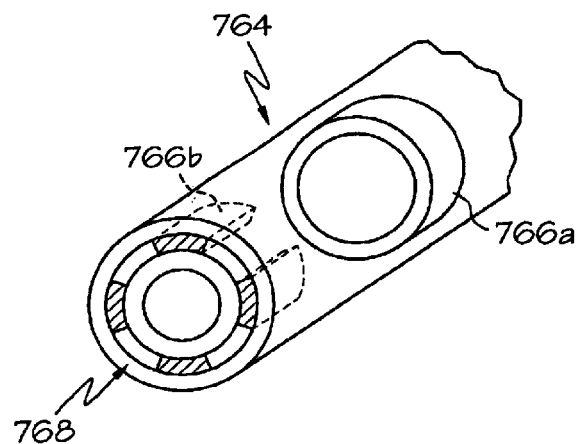
FIG. 7E is a perspective view of a tube rolled from the composite sheet of FIG. 7D.

In an alternative embodiment, stent 50 may comprise a single composite hypotube having plastically-deformable longitudinal stripes that is cut to form a seamless stent. FIGS. 7A–8B illustrate various methods for forming a composite hypotube. As shown in FIG. 7A, a composite sandwich sheet 750 may comprise a lower layer 752 and upper layer 754 comprising superelastic material, such as nitinol, and a plurality of continuous longitudinal strips 756a–d comprising plastically deformable material. Plastically deformable stripes 756a–d may comprise high density metal such as Pt, Ta, Au, Pd, W and the like, which provide improved visibility under x-ray imaging. Stiffer metals, such as W, may be preferred to add more stiffness to the composite. Each strip 756a–d may comprise the same material, different materials, or alternating stripes of two or more different materials may be used, such that, for example, stripes 756a and 756c may comprise a first material, while stripes 756b and 756d comprise another. The thickness of individual stripes 756a–d, spaces 757a–c between the stripes, and overall number of stripes, in conjunction with the materials of the stripes, all may be varied as desired to obtain desired composite characteristics. Stripes may be longitudinal as shown in FIGS. 7A–7C, or transverse as shown in FIGS. 7D–7E, and may be continuous or broken. Thus, for example, stripes 756a–d may extend from end to end of lower sheet 752, or may only be present at the ends and not in the middle, or in selected longitudinal sections to provide area of balloon-expandability only where desired. Regardless of whether the stripes are continuous or broken, or longitudinal or transverse, all of the embodiments described herein can be described as comprising a layer of plastically deformable material in a non-continuous distribution sandwiched between layers of superelastic materials.

Composite sandwich sheet 750 may be fabricated by depositing stripes 756a–d on lower layer 752 or upper layer 754, the two layers placed together with the stripes in between, and then the sandwich rolled to a final thickness. The rolled sandwich may then be formed into a tube 751 with the ends joined together at weld 758, as shown in FIG. 7B. Layers 752 and 754 may be fused together with stripes 756a–d in between using a hot isostatic press prior to rolling. Stripes 756a–d may be deposited by electroplating, ion beam deposition, plasma spray, laser-assisted deposition, or any method known in the art. In particular, electro-polishing the surface of nitinol onto which the stripes are to be deposited (to remove oxides from the metal surface) has been found to be desirable prior to the deposition step. For gold electroplating, the use of an acid-based gold strike process is preferred, such as is described in U.S. Pat. No. 09,227,407 by Steven Taskovics et al., filed on Jan. 8, 1999, assigned to the common assignee of this invention and incorporated herein by reference.

In another embodiment, shown in FIG. 7C, longitudinal stripes 756a–d may be electroplated onto an inner hypotube 760 and the striped inner hypotube placed inside an outer hypotube 762. The tube may then be drawn, as is known in the art, to create a continuous hypotube similar to that shown in FIG. 7B (absent weld 758). The non-continuous intermediate layer formed by stripes 756a–d allows for areas of nitinol to nitinol contact between the stripes to provide support during the drawing process, which is an advantage over the use of a continuous intermediate layer.

Although shown in FIGS. 7A–7C with stripes 756a–d that run longitudinally, the stripes may also run transversely, as shown in FIGS. 7D and 7E. Transverse stripes 756e and 756f may be formed between lower and upper sheets 752 and 754 respectively using the sheet fabrication process as shown in FIG. 7D and describe above with respect to FIGS. 7A–7B, or may be formed using the hypotube process as described above with respect to FIG. 7C. The final tube structure 764 may thus comprise a seamless tube, as shown in FIG. 7E, if manufactured using hypotubes and drawing the assembled hypotubes, or may have a longitudinal weld similar to weld 758 shown in FIG. 7B, if created as a rolled sheet and then joined at the ends. In either case, tube 764 comprises one or more longitudinal sections 766a and 766b comprising an inner ring of plastically deformable material. As with the longitudinal stripes, the transverse stripes may be continuous or broken, such as stripe 756f, which is broken into four pieces, $756f_{i-iv}$ which results in a broken ring 766b of plastically deformable material. Thus, as shown in FIG. 7E, the resulting ring 766b essentially comprises a set of longitudinal stripes or plastically deformable material present only on end section 768 of tube 764.

Figure 8A:
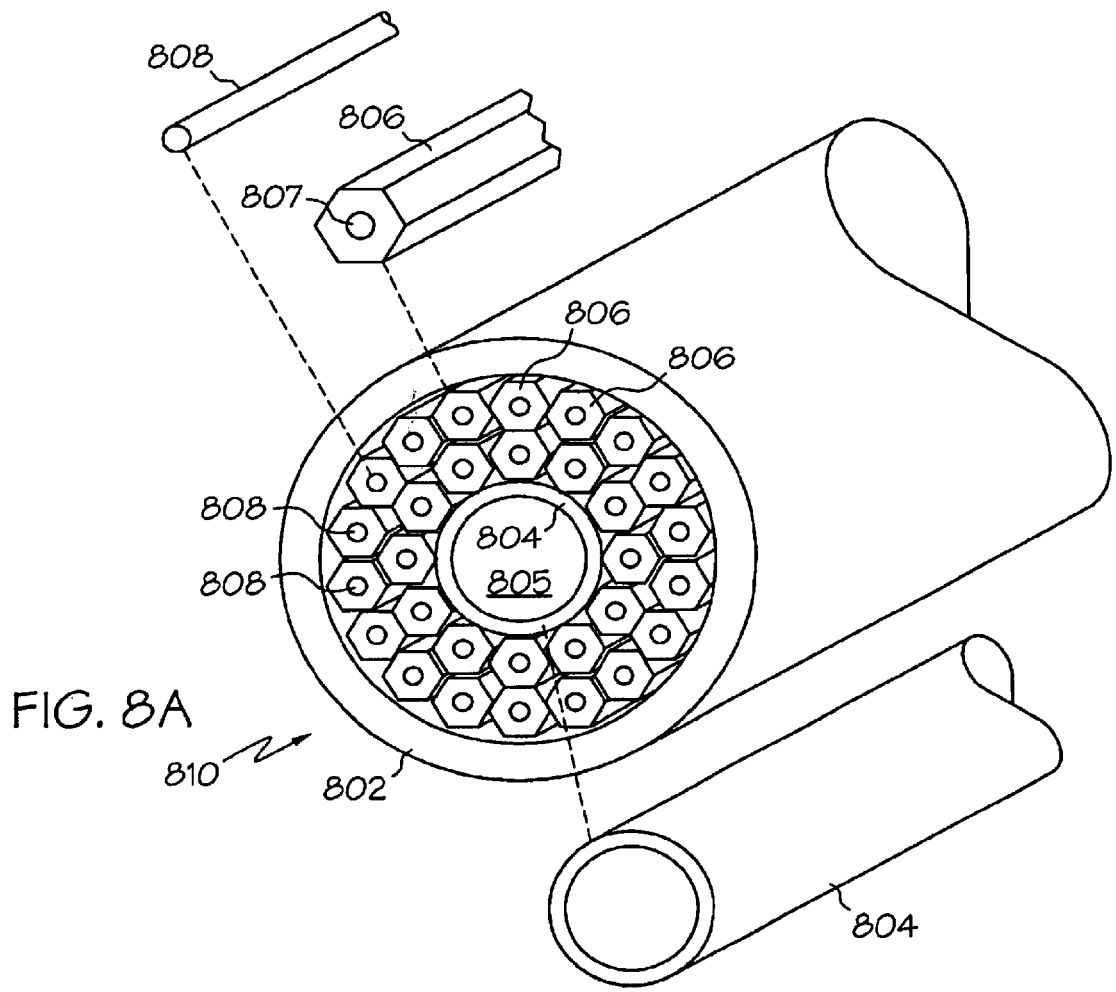
FIG. 8A is a perspective view of an exemplary assembled composite tube and its individual components for making an exemplary stent embodiment of the present invention, prior to a tube drawing step.
Figure 8B:
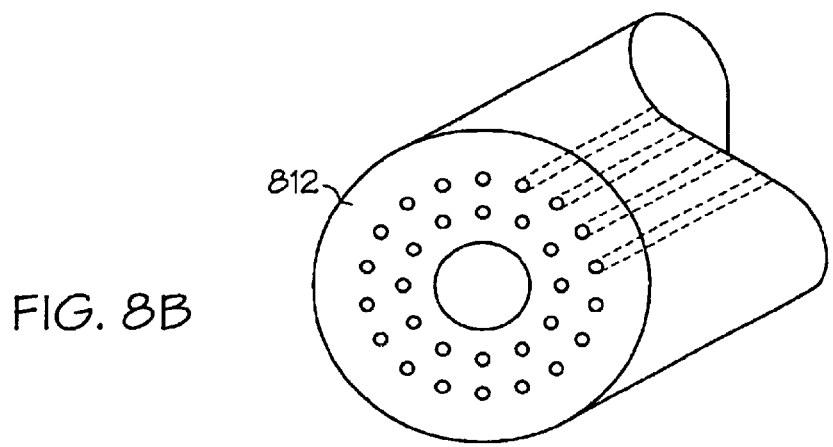
FIG. 8B is a perspective view of a tube of FIG. 8A after the tube drawing step.

Yet another process for forming a composite hypotube is illustrated with respect to FIGS. 8A and 8B, using technology similar to technology used in the formation of superconducting wires. A relatively large diameter superelastic hypotube 802 and a relatively smaller diameter superelastic hypotube 804 are positioned concentrically and a number of even smaller diameter superelastic tubes 806 are packed between tubes 802 and 804, as shown in FIG. 8A. Into the core 807 of each tube 806 is placed a plastically deformable wire 808. Heat and pressure, such as in a hot isostatic press, may be used to consolidate the assembly 810 into a bonded structure. Then assembly 810 is drawn to a desired diameter, leaving the final tube structure 812 shown in FIG. 8B having longitudinal cylindrical portions of plastically deformable material embedded therein. A sacrificial center core (not shown) may be used within the center 805 of tube 804 to assist in drawing tube 812. The sacrificial center core may then be removed at a later time by etching or a "pull to shrink" process as is known in the art. Wires 808 may also be used in place of stripes 756 or 756a–d when forming the composite using the processes described with respect to FIGS. 7A–7E. Although shown in FIG. 8A as having a hexagonal cross-section, tubes 806 may have any geometric cross-section known in the art. In yet another embodiment, the tube structure 812 shown in FIG. 8B may be created by starting with a thick-walled hypotube (not shown), drilling longitudinal holes in the hypotube and filling them with wires 808, and then drawing the assembled composite to create structure 812.

It should be noted that although described herein with respect to the use of superelastic and plastically deformable composite materials, the above composite processes may also be used for forming composite materials using only plastically deformable materials. For example, instead of lower and upper sheets 752 and 754 or inner and outer hypotubes 760 and 762, respectively, comprising a superelastic material such as nitinol, these components may comprise stainless steel, a cobalt alloy, or the like. The provision of stripes of other materials may thus be used to provide improved radiopacity, increased or decreased stiffness, or some other desired material property. Furthermore, for composites of plastically deformable and superelastic materials, the choice of plastically deformable material and the amount thereof in the composite can be chosen to create a hybrid device that is both plastically deformable and superelastic as described herein, or can be chosen merely to enhance radiopacity without significantly affecting the superelastic properties of the superelastic material.

Figure 7F:
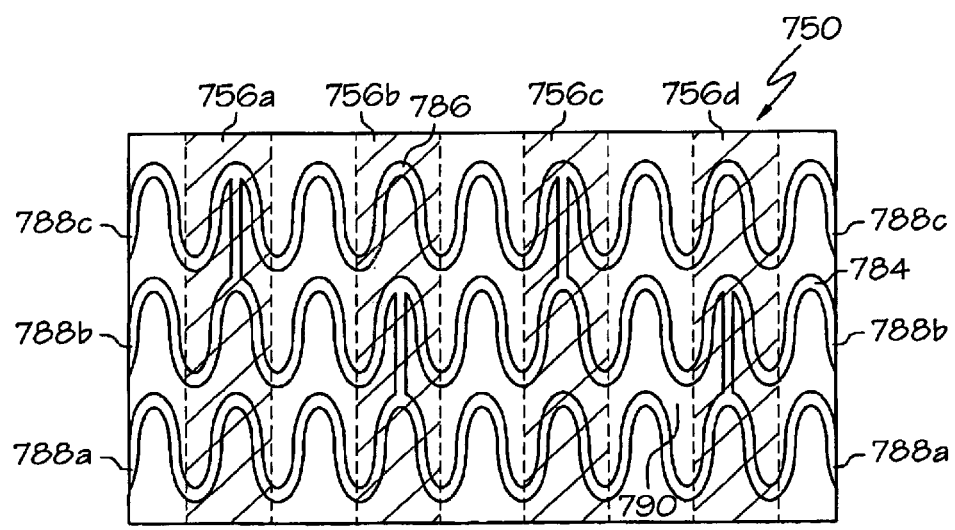
FIG. 7F is a plan view illustration of a pattern to be cut on the composite sheet of FIG. 7A.

Referring now to FIG. 7F, to form the stent or vena cava filter, the resulting composite sandwich 750 (after rolling) may then be cut by etching or cutting as is known in the art, in a pattern 784 corresponding to the desired architecture of the device, such as the zig-zag architecture shown in FIG. 7F. The pattern may preferably be aligned so that the features of the architecture desired to be plastically deformable, such as every other upwardly-pointing apex 786, as shown in FIG. 7F, are aligned with plastically deformable stripes 756a–d within composite sheet 750. After cutting, the resulting flat pattern 784 may comprise an apertured well such as a wall having a plurality of aperture or cells 790. The apertures or cells 790 extend completely through the wall. After cutting, the resulting flat pattern 784 may then be rolled into a tubular shape and ends 788a, 788b, and 788c welded together as 788a—788a, 788b—788b, and 788c—788c to form the desired device. In the alternative, the tubular composite shown in FIGS. 712 or 712 may be cut in their tubular form to create the device. Although shown in FIG. 7F with the stripes oriented longitudinally with respect to the cylindrical orientation of the device, the stripes may also be transverse as shown in FIGS. 71 and 7E.

Thus, in the embodiments using a composite sheet or tube, the plastically deformable section comprises a combination of plastically deformable and superelastic material, similar to the embodiments shown in FIGS. 3A–C. In each embodiment, the critical high strain area can comprise plastically deformable or superelastic sections. If all the high strain areas are superelastic, the device will be fully self-expanding. If all the high strain areas are plastically deformable, the device will be balloon expandable only. According to the present invention, some high strain areas comprise superelastic sections and some comprise plastically deformable areas such that the device is self-expanding with the ability to be fined tuned by balloon expansion.

In each of the embodiments shown herein, but referring now to FIGS. 4D–4F, the device has a first constrained diameter $D_1$ for introduction into a body lumen, a second fully-self-expanded diameter $D_2$ after initial deployment in a body lumen, and a third fully-forcibly-expanded diameter $D_3$ after full forced expansion, such as with a balloon. $D_3$ is greater than $D_2$, which is greater than $D_1$.

To deploy an endoluminal device of this invention in a body lumen, the method comprises first introducing the device into the body lumen with the device radially constrained in a first configuration, as shown in FIGS. 3A, 4A, 4D, and 5A. As shown in FIG. 4D, the device in this configuration has a first diameter $D_1$. This radially constrained configuration typically arises after a constraining force F, is applied to the stent to collapse the device. The device in its constrained configuration is then typically loaded within an introducer for introduction into the body of a recipient.

After the introducer reaches the desired deployment position, the device is released from the sheath or other constraining means within the introducer, allowing the device to self-expand into a second configuration approaching or equal to the full-self-expanded configuration shown in FIGS. 3B, 4B, and 5B. As shown in FIG. 4E, this fully-self-expanded configuration has a second diameter $D_2$ greater than the first diameter $D_1$.

Then, optionally, a balloon is inserted within the circumference of the device and inflated to forcibly expand at least longitudinal portions of the device to a third configuration. As further described below, this third configuration may range between greater than the second configuration and less than or equal to the fully-forcibly-expanded configuration shown in FIGS. 3C, 4C, and 5C.

As shown in FIG. 4F, the fully-forcibly-expanded configuration has a third diameter $D_3$ greater than the second diameter $D_2$. During the forcible expansion step, the balloon may forcibly expand the device into a fourth, overexpanded configuration having a diameter greater than the third diameter, as the self-expanding section of the stent may become expanded past its resting state. After the balloon is deflated, however, the device will relax back to the third configuration.

It should be noted that in actual deployment of a device in the body, that the deployment method may be terminated after the device expands to the second configuration if the diameter in that configuration is deemed adequate to perform the desired function. In other instances, it may be necessary to fully expand the device into the third configuration. In most instances, however, the desired configuration may be intermediate the second and third configurations. Likewise, it should also be noted that the body lumen may partially constrain all or part of the device from fully expanding even to the fully-self-expanded configuration. Thus, the second configuration may comprise an expanded configuration wherein the device or portions of the device have a diameter somewhat less than $D_2$. Thus, the device in its finally deployed configuration may have a single diameter throughout, where that diameter ranges from somewhat less than $D_2$ to less than or equal to $D_3$, or some longitudinal sections may have a diameter as small as somewhat less than $D_2$, other sections a diameter as great as $D_3$, and still other sections a diameter intermediate $D_2$ and $D_3$.

The advantage of the present invention is that it can in fact be tailored to conform to the anatomy of the lumen in which it is deployed by deforming the plastically deformable section of the device without changing the characteristics of the superelastic section of the device. Thus, the invention comprises a self-expanding device that can be "fine tuned" by deforming the plastically deformable section to achieve optimum sizing. This may be particularly useful for adapting a device to a lumen having a non-round, more oval cross-section, an application for which self-expanding devices generally are considered deficient because of their tendency to deploy with a round cross-section. Additionally, to the extent that the plastically deformable materials can be selected having better x-ray visibility than superelastic materials, devices of the present invention may also have increased x-ray visibility without the need for adding special radiopaque markers.

Devices of this invention may be manufactured by any of the typical means known in the art, consistent with this invention. For example, filamentary devices may be wound upon a mandrel or formed into a sheet, then rolled into a cylindrical shape. Similarly, cut tube devices may be cut in sheet form and then rolled, or formed as a tube and cut in their tubular configuration.

Figure 9:
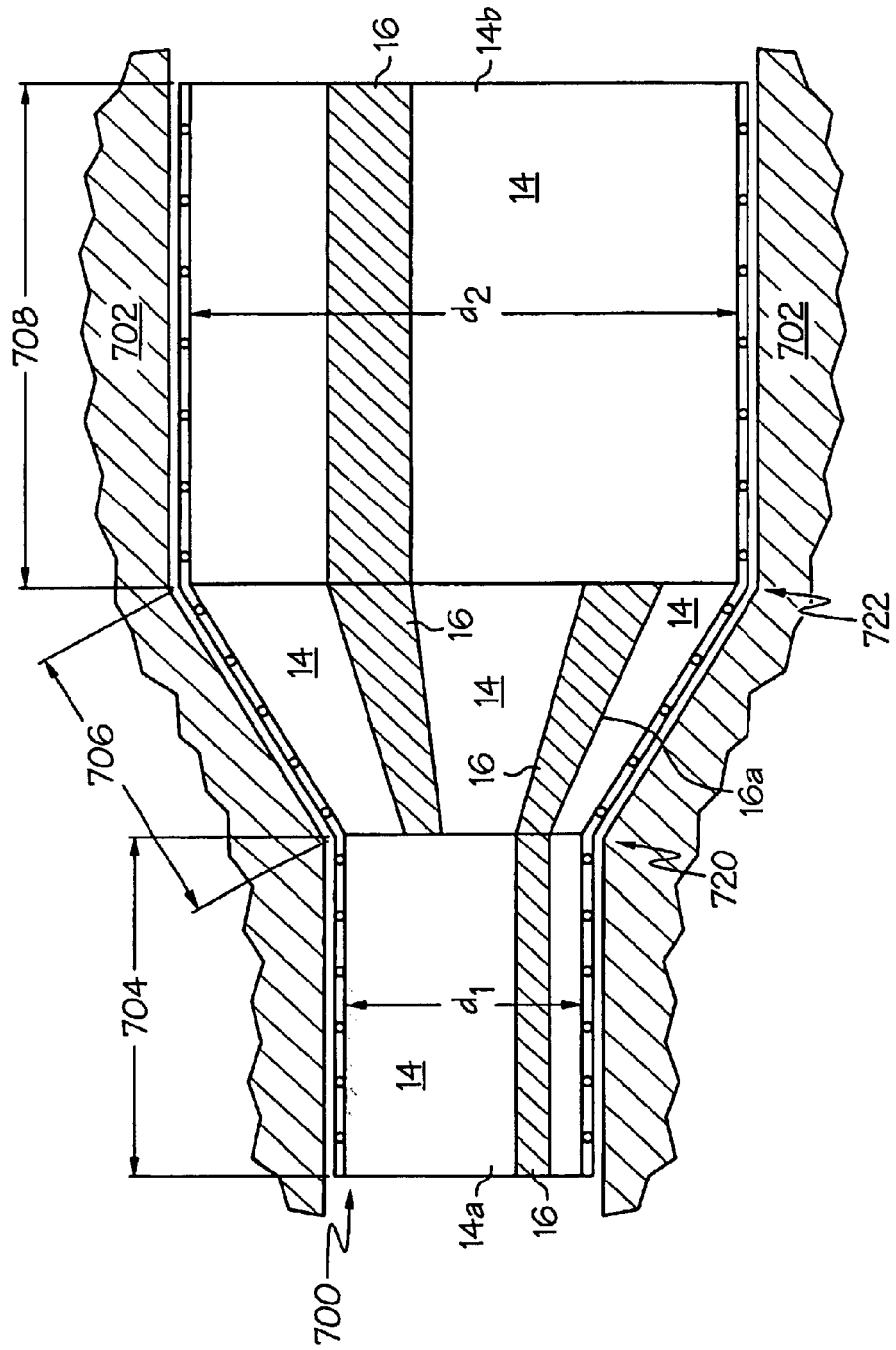
FIG. 9 is a longitudinal section illustration of an exemplary prosthesis deployed in a lumen.

Although described above with respect to devices wherein the superelastic section and the plastically deformable section extend longitudinally along the length of the device, each section may instead comprise tubular portions axially attached to one another, as shown in FIG. 9. FIG. 9 depicts device 700 deployed within a lumen 702 having a small diameter section 704, a tapered section 706, and a large diameter section 708. A first superelastic section 14a having a first self-expanded diameter $d_1$ is deployed in section 704 and a second superelastic section 14b having a second self-expanded diameter $d_2$ is deployed in section 708. It should be understood that the deployed self-expanded diameters $d_1$ and $d_2$ as constrained by lumen 702 may be slightly less than the fully self-expanded diameters (not shown) of section 14a and 14b. It should also be understood that portions 704 and 708 of lumen 702 may also be tapered somewhat, and that the self-expanded diameters may be variable from a more-lumen-constrained diameter at one end to a less-lumen-constrained diameter at the opposite end. Plastically deformable section 16a is deployed within tapered section 706. The presence of plastically deformable section 16a allows the taper of the device to be tailored specifically to the tapered diameter of tapered section 706 of lumen 702 such that the diameter of section 16a is essentially $d_1$ at first end 720 and essentially $d_2$ at second end 722. As used herein "essentially" means that the diameter at each end may be slightly greater or less than the respective diameter of the adjacent section. Of course, although shown in FIG. 9 with a plastically deformable section between two superelastic sections, the device may comprise two plastically deformable sections having a superelastic section therebetween, or any multiple of plastically deformable and superelastic sections, including merely one of each section.

Plastically deformable section 16 in device 700 may comprise all plastically deformable materials, or may be a combination of plastically deformable materials and superelastic materials as described above. For example, device 700 may comprise a zig-zag architecture as shown in FIGS. 3A–3C and 6, comprising one or more filaments 15 wherein section 16a comprises plastically deformable material 320 that constrains at least portions of the filaments. Similarly, device 700 may comprise a cut tubular device in which section 16a comprises a composite portion of plastically deformable material and superelastic whereas sections 14a and 14b comprise superelastic material only, such as shown in FIG. 7E. Depending on the difference in diameter between sections 704 and 708 of lumen 702, superelastic sections 14a and 14b may have the same fully-self-expanded diameter, or section 14b may have a larger fully-self-expanded diameter than section 14b. Thus, sections 14a, 14b, and 16 may comprise discrete sections attached together by any means known in the art, such as by suturing, welding, brazing, adhesively bonding, or attachment to a common graft. Sections 14a, 14b, and 16 may also be attached to one another by any of the means described in the aforementioned U.S. patent application Ser. No. 09/442,165. In the alternative device 700 may comprise a unitary superelastic construction in which sections 14a and 14b are identical in construction and fully-self-expanded diameter, and section 16 merely comprises constraining plastically deformable material combined with the superelastic material as described herein.

Finally, device 700 may comprise a device in which each of sections 14a, 14b, and 16a themselves comprise combinations of superelastic and plastically deformable subsections wherein each superelastic subsection and plastically deformable subsection extend longitudinally along the length of each section as shown, for example, in FIG. 1. Thus, section 16a may merely be relatively more plastically deformable than sections 14a and 14b. For example, as shown in FIG. 9, section 16a comprises more plastically deformable subsections than in sections 14a and 14b. Stated another way, section 16a has a higher ratio of plastically deformable material to superelastic material than in sections 14a and 14b.

Whereas device 700 as shown in FIG. 9 has a plastically deformable section in the middle, in some instances it may be preferable to have plastically deformable sections only on the ends. For example, as shown in FIG. 10, device 100 has plastically deformable sections 1002 and 1003 on opposite ends and a superelastic section 1004 in the center. For simplicity, device 1000 is depicted as a solid cylinder in side view with each section clearly defined, but is understood to have any filamentary or cut tubular architecture known in the art, with each section not necessarily definable from external viewing. This configuration is particularly useful to address an existing problem with self-expanding stents that "jump off" the delivery catheters during deployment. The configuration of device 1000 assures that the ends stay in place on the balloon catheter until expanded to implant the device precisely where desired. As shown in FIG. 10, the device ends have longitudinal stripes 1006 of plastically deformable material, such as what would result on end 768 of tube structure 764 shown in FIG. 7E, for example, after a cutting or etching step to create the device architecture, as depicted in FIG. 7F. This allows the ends of the device to be tapered or flared as necessary to conform to the anatomy of the patient.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. An endoluminal device comprising:
 a framework having a central longitudinal axis, the framework forming a wall having a plurality of cells, the wall having a constant thickness, the cells extending through the thickness of the wall, the framework comprising a first section having a thickness and a second section having a thickness, the first section consisting of a superelastic material, the second section comprising a combination of a first portion of superelastic material and a second portion of plastically deformable material, the second portion being a constant distance from said central longitudinal axis along the length of the second section, the thickness of the first section being equal to the thickness of the second section.

2. The device of claim 1, wherein the portion of plastically deformable material has a greater x-ray visibility than the first section.

3. The device of claim 1, wherein each said superelastic section comprises a precision-cut sheet or a longitudinally severed precision-cut tube.

4. The device of claim 1, wherein the plastically deformable portion constrains the superelastic portion of the second section 5. The device of claim 4, wherein said combination is selected from a group consisting of: plastically deformable material plated onto said superelastic material, a plastically deformable hypotube overlaid onto said superelastic material, ion implantation of said plastically deformable material into said superelastic material, and a composite comprising said deformable material and said superelastic material.

6. The device of claim 4, wherein the combination further comprises a third portion of superelastic material, wherein the second portion of plastically deformable material is sandwiched between the first and third portions of the superelastic material.

7. The device of claim 4, wherein the plastically deformable material is gold.

8. The device of claim 1 having a first constrained diameter, a second fully-self-expanded diameter, and a third fully-forcibly-expanded diameter, wherein said third diameter is greater than said second diameter and said second diameter is greater than said first diameter.

9. The device of claim 1, wherein said superelastic material comprises nitinol and said plastically deformable material is selected from the group consisting of: gold, platinum, tantalum, titanium, stainless steel, tungsten, palladium, a nickel alloy, a titanium alloy, a cobalt alloy, and a combination thereof.

10. The device of claim 1, wherein the device is selected from the group consisting of: a stent and a vena cava filter.

11. The device of claim 1, wherein said at least one superelastic section comprises a first tubular section and said at least one plastically deformable section comprises a second tubular section.

12. The device of claim 11, wherein the first tubular section consists essentially of a superelastic material alone and the second tubular section consists essentially of plastically deformable material alone.

13. An endoluminal device comprising:
a framework cut from a tube having a central longitudinal axis, the framework comprising a first section having a thickness and a second section having a thickness, the first section consisting of a superelastic material, the second section comprising a combination of a first portion of superelastic material and a second portion of plastically deformable material, the second portion being a constant distance from said central longitudinal axis along the length of the second section, the thickness of the first section being equal to the thickness of the second section.

14. The device of claim 13, wherein the second portion has a greater x-ray visibility than the first section.

15. The device of claim 13, wherein the plastically deformable portion constrains the superelastic portion of the second section.

16. The device of claim 15, wherein said combination is selected from a group consisting of: plastically deformable material plated onto said superelastic material, a plastically deformable hypotube overlaid onto said superelastic material, ion implantation of said plastically deformable material into said superelastic material, and a composite comprising said deformable material and said superelastic material.

17. The device of claim 15, wherein the combination further comprises a third portion of superelastic material, wherein the second portion of plastically deformable material is sandwiched between the first and third portions of the superelastic material.

18. The device of claim 15, wherein the plastically deformable material is gold.

19. The device of claim 13, having a first constrained diameter, a second fully-self-expanded diameter, and a third fully-forcibly-expanded diameter, wherein said third diameter is greater than said second diameter and said second diameter is greater than said first diameter.

20. The device of claim 13, wherein said superelastic material comprises nitinol and said plastically deformable material is selected from the group consisting of: gold, platinum, tantalum, titanium, stainless steel, tungsten, palladium, a nickel alloy, a titanium alloy, a cobalt alloy, and a combination thereof.

21. The device of claim 13, wherein the device is selected from the group consisting of: a stent and a vena cava filter.

22. An endoluminal device comprising:
a framework having a central longitudinal axis, the framework forming an apertured wall, the apertured wall having a constant thickness, the apertures extending through the thickness of the wall, the framework comprising a first section having a thickness and a second section having a thickness, the first section consisting of a superelastic material, the second section comprising a combination of a first portion of superelastic material and a second portion of plastically deformable material, the second portion and being a constant distance from said central longitudinal axis along the length of the second section, the thickness of the first section being equal to the thickness of the second section.

* * * * *